US011269174B2

(12) United States Patent
Lust et al.

(10) Patent No.: US 11,269,174 B2
(45) Date of Patent: Mar. 8, 2022

(54) ENDOSCOPIC IMAGING

(71) Applicant: Honeywell International Inc., Morris Plains, NJ (US)

(72) Inventors: Lisa Lust, Plymouth, MN (US); Mary Salit, Plymouth, MN (US)

(73) Assignee: Honeywell International Inc., Charlotte, NC (US)

( * ) Notice: Subject to any disclaimer, the term of this patent is extended or adjusted under 35 U.S.C. 154(b) by 475 days.

(21) Appl. No.: 16/242,775

(22) Filed: Jan. 8, 2019

(65) Prior Publication Data
US 2020/0214541 A1  Jul. 9, 2020

(51) Int. Cl.
*G02B 23/24* (2006.01)

(52) U.S. Cl.
CPC ......... *G02B 23/2469* (2013.01); *G02B 23/24* (2013.01)

(58) Field of Classification Search
None
See application file for complete search history.

(56) References Cited

U.S. PATENT DOCUMENTS

| | | | | |
|---|---|---|---|---|
| 4,070,092 A * | 1/1978 | Burns | ................... | G02F 1/3137 385/132 |
| 5,502,781 A * | 3/1996 | Li | ...................... | G01R 33/0327 385/132 |
| 5,807,264 A * | 9/1998 | Paltieli | ................... | A61B 5/411 600/477 |
| 5,956,447 A * | 9/1999 | Zel'Dovich | ............ | G02B 23/26 385/116 |
| 2008/0112596 A1* | 5/2008 | Rhoads | .................... | G07D 7/12 382/115 |
| 2008/0132762 A1* | 6/2008 | Melville | ............... | A61B 1/0055 600/146 |
| 2014/0233028 A1* | 8/2014 | Englund | ............... | G01J 3/0229 356/303 |
| 2014/0235948 A1* | 8/2014 | Mahalati | ............ | A61B 1/00165 600/160 |
| 2015/0015879 A1* | 1/2015 | Papadopoulos | ...... | G02B 6/0288 356/301 |
| 2016/0345813 A1* | 12/2016 | Jang | ................... | A61B 1/00009 |
| 2017/0153440 A1* | 6/2017 | Caravaca-Aguirre | ...... | G02B 23/26 |
| 2018/0143373 A1* | 5/2018 | Cizmár | ................ | G02B 6/0288 |

* cited by examiner

*Primary Examiner* — Timothy J Neal
(74) *Attorney, Agent, or Firm* — Brooks, Cameron & Huebsch, PLLC

(57) ABSTRACT

Sub-diffraction endoscopic modal imaging systems and methods are disclosed herein. A single multi-mode fiber endoscope incorporated into a modal imaging system can facilitate the imaging of inner portions of a patient's body at a quantum-limited resolution. One method of sub-diffraction endoscopic modal imaging includes collecting incoming radiation with a multi-mode fiber, separating the output into multiple modes, and measuring an energy level of each mode to construct an image of the received incoming radiation.

20 Claims, 3 Drawing Sheets

ENDOSCOPIC IMAGING

TECHNICAL FIELD

The present disclosure relates to super-resolution sub-diffraction endoscopic imaging.

BACKGROUND

Endoscopy is a medical imaging technique that enables the examination of organs and cavities inside the body. The method involves inserting a tubular instrument called an endoscope into the desired organ or cavity. Such devices are useful because they allow a medical practitioner to view an inside portion of a patient's body without making incisions or through minimally invasive surgeries that require only small incisions.

The traditional endoscope has been comprised of a bundle of multiple single-mode fibers, wherein each of the fibers forms a pixel on a reconstructed image. Therefore, a high quantity of fibers have been required to feasibly reconstruct the image. However, using a high quantity of fibers corresponds to a large bundle diameter. Hence, an endoscope comprised of a bundle of single-mode fibers by necessity has a large diameter on the order of millimeters, which is problematic in some types of operations. Endoscopes with smaller diameters are ideal, because they are easier to insert into a patient's body and, therefore can be less damaging to the body and can be used in more areas.

Recently, efforts have been made to transition from a bundle of single mode fibers to a single, multi-mode fiber to achieve higher image resolution and smaller device diameter. Current methods of endoscopic imaging using a single multi-mode fiber involve passing light from a source down into the desired imaging subject, reflecting the light into a fiber of the endoscope, and sending the radiation toward detectors to reconstruct the image. In other words, current methods of single multi-mode fiber endoscopic imaging have utilized direct imaging.

However, passing an image through a single multi-mode fiber using this method causes distortion, called mode mixing and the output of the fiber takes the form of a speckle pattern. Methods of eliminating mode mixing have been developed, but still suffer from limited resolution owing to the Rayleigh Criterion.

DETAILED DESCRIPTION

Figure 1:
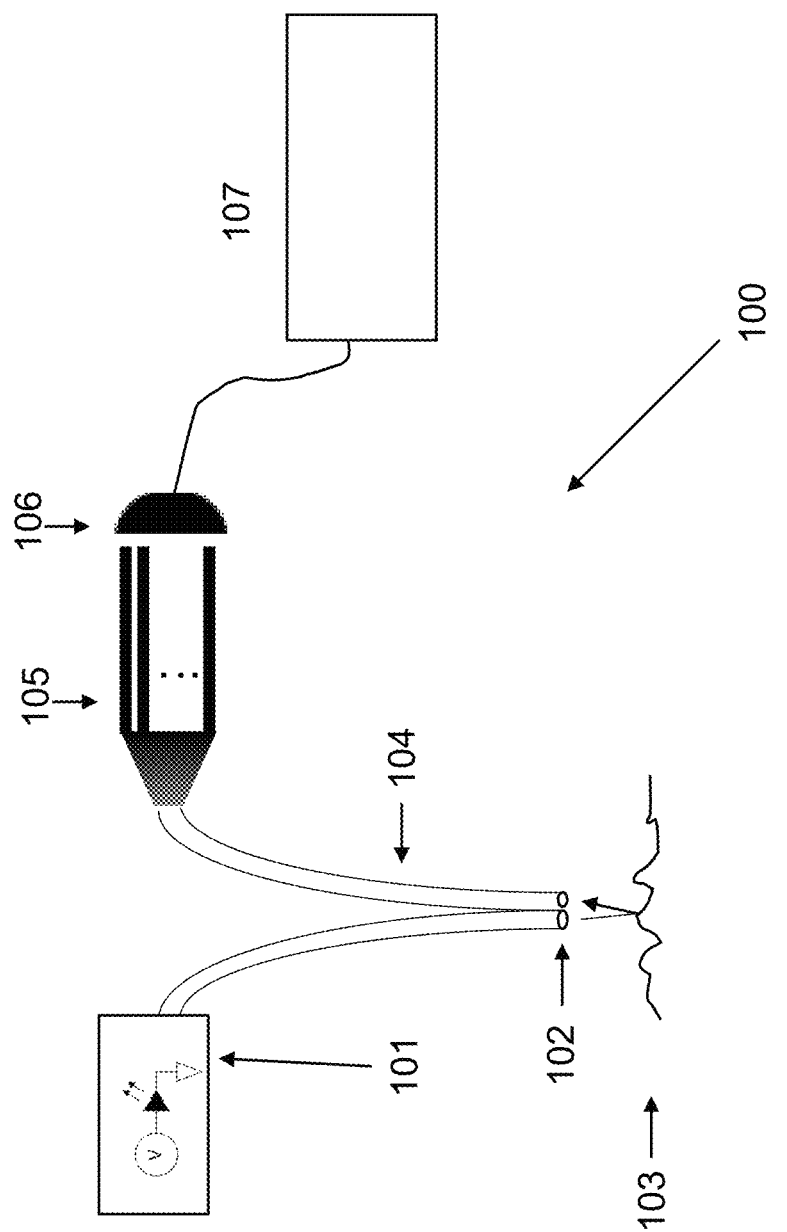
FIG. 1 illustrates an endoscopic modal imaging system in accordance with one or more embodiments of the present disclosure.

As discussed above, the current methods of endoscopic imaging suffer from either limited resolution due to the Raleigh Criterion or excessively large device diameters. Utilizing an alternative method of imaging, as discussed in the present disclosure, can provide a technique to vastly improve the resolution of an image for a single multi-mode fiber without adding any in-body elements.

Thus, these techniques can allow users to successfully image nerves, small tissues, and other microscopic elements of a patient's body through an endoscope. Such techniques can be implemented using as few as one multi-mode fiber as opposed to multiple single-mode fibers, thus minimizing the total diameter of the endoscope. The apparatuses and techniques described herein can successfully image inner parts of a body at the sub-diffraction level using a single multi-mode fiber.

The present disclosure may have broad applications to the field of endoscopic imaging whereby radiation can, for example, be collected using a multi-mode fiber, and separated on a modal basis using a mode separating structure. The present disclosure can, for example, provide a technique by which the micro elements of the human body can be imaged endoscopically using a single multi-mode fiber.

As discussed above, in previous approaches, bundles of single-mode fibers have been used. This approach not only increases the diameter of the device, but also produces an image with a classically-limited resolution.

However, embodiments of the present disclosure can provide methods and apparatuses by which a single multi-mode fiber projected onto a mode separating structure, such as a spatial mode demultiplexer, can be used to reconstruct a quantum-resolution image. As such, embodiments of the present disclosure can improve a wide variety of endoscopic devices whereby a direct imaging approach could be taken (e.g., focusing radiation on an image plane whereby the radiation intensity/power is recorded).

The present disclosure can provide methods and apparatuses by which complex sources may be imaged. In previous approaches, only the distance between a few point sources could be determined. However, the embodiments of the present disclosure can provide methods and apparatuses by which an N point source image may be generated.

As described herein, a "source image" can be derived from imaging of the "incoming radiation" which enters the apparatus through a single multi-mode fiber. As used herein, the term "incoming radiation" can be used interchangeably with "incoming photons" and/or "incoming light".

Embodiments of the present disclosure can treat the source images as a collection of independent individual point sources. Such embodiments can use the incoherent nature of the image sources to define mathematical distributions of the image modes.

The parameters of these modal distributions define the location of the point source from which they originated. The present disclosure provides a description whereby full imaging may be realized based upon using a mechanism (e.g., a spatial mode demultiplexer, photonic lantern, or optical grating) to separate the incoming radiation into its modes.

A mode in this context can be considered a description of the spatial confinement of the electromagnetic energy corresponding of one of the waveguide's eigenfunctions. The parameters of these modal distributions define the location of the point source from which they originated.

In such a technique, spatial coordinates of any point source of the incoming radiation are described in a coordinate system based upon the hypothetical image plane. The measurement of modes can then be used to determine the location of the point sources on the hypothetical image plane.

A method of operating a sub-diffraction endoscopic imaging device can, for example, include collecting incoming radiation with a multi-mode fiber, separating the output of the multi-mode fiber into multiple modes, and measuring an energy level of each mode to construct an image of the received incoming radiation. The output of the multi-mode fiber can be deconvoluted using the transfer matrix method. This method essentially calculates the statistical distributions of the modes based on the multi-mode fiber structures and assigns the average mode of each distribution to reconstruct the image.

In such an embodiment, each mode of radiation can be routed through a waveguide from elements of an input imaging array to elements of an output array. The radiation can then be directed from the output array elements to one or more detector array elements. The modal distribution can be analyzed to discern an image from which the modal distribution originated, wherein the modal distribution is an output of one or more photon detectors placed at an end of the multi-mode fiber.

This disclosure also provides a description whereby sub-diffraction modal imaging may be achieved through an endoscopic system having a single multi-mode fiber that receives incoming radiation. An end of the multi-mode fiber can be placed so that it images an inner portion of a patient's body.

Any light source of limited coherence may be used to illuminate the relevant portion of the patient's body. Alternatively, illumination from fluorescencing emitters introduced into the patient may be used if more convenient. The system can also include a mode separating structure (for example, a spatial mode demultiplexer) for separating the received incoming radiation into modes and at least one detector element for measuring the energy level of each mode to construct an image of the received incoming radiation.

In some embodiments, the detector elements can form an array. Optical waveguides can connect elements of the input imaging array to elements of the output array.

In such embodiments, the image's accuracy can be theoretically bounded by the quantum resolution limit, but in practice, experimental limitations may define the accuracy.

Similarly, the present disclosure includes method embodiments for sub-diffraction modal imaging. Such a method can, for example, be a method of operating an endoscopic imaging device, comprising collecting incoming radiation with a multi-mode fiber, separating an output of the multi-mode fiber into multiple modes, and measuring an energy level of each mode to construct an image of the received incoming radiation.

These embodiments are described in sufficient detail to enable those of ordinary skill in the art to practice one or more embodiments of this disclosure. It is to be understood that other embodiments may be utilized and that mechanical, electrical, and/or process changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure and should not be taken in a limiting sense.

To understand modal imaging, it is useful to describe radiation reflected or emitted from a target arising from many independent, incoherent, and weakly coherent point sources. Each point source generates a Poisson distribution in terms of its photon number and, thus, its energy distribution.

Electromagnetic energy can be defined by these modes, which are simply eigensolutions to the propagation equations. Measuring and mapping the electromagnetic energy in a two dimensional modal basis (q, r) forms a composite of Poisson distributions across the space.

To derive this modal expression in an imaging device (e.g., an endoscope) of aperture, D, first we start with the analysis used in conventional imaging.

A Gaussian point spread function (PSF) can be used to model the effect of the objective light collection lens for this analysis. The technique is not limited to a Gaussian but can use any PSF of the system.

$$|\psi(x, y)\rangle = \int_{-\infty}^{\infty} dx \int_{-\infty}^{\infty} dy \varphi(x, y) |x, y\rangle$$

$$\psi(x, y) = \left(\frac{1}{2\pi\sigma_x\sigma_y}\right)^{1/2} \exp\left(-\frac{x^2}{\sigma_x^2} - \frac{y^2}{\sigma_y^2}\right)$$

The dispersion is wavelength, λ, dependent given by $$\sigma_x = \sigma_y \sim \frac{2f\lambda}{D} \sim$$

where D is the diameter of an optical component (e.g., objective lens of an endoscope) with focal length f. Directly imaging the radiation on a focal plane of light sensing pixels is given by the following expression which generates the conventional Rayleigh limited image.

$$I = (|\psi(x+x_l, y+y_m)\rangle\langle\psi(x+x_l, y+y_m)|)^2$$

In endoscopic modal imaging, the radiation can be captured by the imager's multi-mode fiber instead of being focused on a focal plane array of light sensing pixels. In such implementations, this maps the incoming radiation onto the waveguide's modal basis. For a traditional fiber optic this maybe LP modes, or Laguerre-Gauss modes. For a rectangular waveguide this is a Hermite-Gaussian basis, $$|\phi_{qr}\rangle = \int\int dx dy \phi_{qr}(x, y) |x, y\rangle$$

$$\phi_{qr}(x, y) = \left(\frac{1}{2\pi\sigma_x\sigma_y}\right)^{1/2} \left(\frac{1}{2^{q+r}q!\,r!}\right)^{1/2} H_q\left(\frac{x}{2\sqrt{\sigma_x}}\right) H_r\left(\frac{y}{2\sqrt{\sigma_y}}\right) e^{-\frac{x^2}{4\sigma_x^2} - \frac{y^2}{4\sigma_y^2}}$$

The function $H_q(x)$ refers to the physicist Hermite polynomial. For optimal results the PSF should be matched and to the waveguide. This demands that the amplitude spread function ASF, where PSF=|ASF|² is close to or the same as the waveguide's fundamental mode. Computing the overlap of the PSF with the waveguide's field distribution indicates how the total energy of the photons is dispersed across the qth and rth modes. The collective modal surface is given by:

$$S(q, r) = \sum_{l=1}^{L} \sum_{m=1}^{M} I_{l,m}(|\langle\phi_{q,r}(x, y) | \psi(x - x_l, y - y_m)\rangle|^2)$$

which can be shown to reduce to a summation of Poisson distributions $$S(q,r) = \sum_{l=1}^{L}\sum_{m=1}^{M} I_{l,m} p_{Q_l}(q) p_{R_m}(r) =$$

$$\sum_{l=1}^{L}\sum_{m=1}^{M} I_{l,m} \frac{1}{q!\,r!} e^{-Q_l} e^{-R_m} Q_l^q R_m^r \quad Q_l = \frac{x_l^2}{4\sigma_x^2} \quad R_m = \frac{y_m^2}{4\sigma_y^2}$$

$$S = P_Q I P_R$$

where the coefficient $I_{lm}$ is indicative of each Poisson's photon population and the mean of each distribution $Q_l$, $R_m$ is given by the maximum likelihood expressions:

$$\hat{Q}_l = \sum_{q=0}^{J\,modes} q\, m_{q,r} = \frac{x_l^2}{4\sigma_x^2} \quad \hat{R}_m = \sum_{r=0}^{K\,modes} r\, m_{q,r} = \frac{y_m^2}{4\sigma_y^2}$$

The photon number $m_{q,r}$ is the collective number of counts from each (q,r) mode counter. The fabrication section of this disclosure will discuss the physical collection of this modal surface.

Next an image reconstruction technique must distinguish each of the individual Poisson parameters ($n_{l,m}$, $Q_l$, $R_m$) in the composite modal graph.

To do this deterministically, a Poisson basis is formed at the discretion of the user. The number modes (i.e. q=0, 1, 2, ... $q_{max}$, r=0, 1, 2, ... $r_{max}$) is determined by the waveguide employed. The average values, Ql, Rm are determined by the physical extent of the waveguide and discretization employed. This is generally determined by the condition number of the resulting matrices $p_{Rm}$ and $p_{Ql}$. These matrices must not be ill-conditioned to tolerate the limiting photon shot noise.

$$p_{R_m}(r) \frac{1}{r!} e^{-R_m} R_m^r \quad R_m = \frac{y_m^2}{4\sigma_y^2}$$

$$p_{Q_l}(q) \frac{1}{q!} e^{-Q_l} Q_l^q \quad Q_l = \frac{x_l^2}{4\sigma_x^2}$$

$$I = [p_{Rm}]^{-1} S [p_{Ql}^T]^{-1}$$

The resolution of the image can be determined by the signal-to-noise ratio (SNR) of the optics path to include the total number of photons $\Sigma l,m$ collected (a function of acquisition time), the system path loss, and detector efficiency. Basic statistics can form a bound of the resolution of this imaging process. The standard deviation of the mean can be defined as:

$$\sigma_{Ql} = \frac{\sqrt{Q_l}}{\sqrt{I_{lm}}} \quad \sigma_{Rm} = \frac{\sqrt{R_m}}{\sqrt{I_{lm}}}$$

Thus, the error in $x_l$ and $y_m$ (the location of $n_{lm}$ photons) can be defined as:

$$\varepsilon_x = \sqrt{4\sigma_x^2} \frac{1}{2} Q_l^{-1/2} \sigma_{Ql} = \frac{\sigma_x}{\sqrt{I_{lm}}} \quad \varepsilon_y = \frac{\sigma_y}{\sqrt{I_{lm}}}$$

The error is still related to the aperture dimension, $\sigma_x = \sigma_y \sim wf\lambda/D$ but dramatically reduced by $I_{lm}$, the number of photons collected over some time interval. In such an embodiment, to achieve, for example, an angular resolution, $\alpha_{res}$, it would be necessary to resolve a spacing of $I_{res}=f\tan(\alpha_{res}/2)$ on the objective image plane (although this plane is never physically realized).

Thus, the error in the modal imager is calculated to be $2\varepsilon < I_{res}$. The variance in $I_{lm}$ is representative of the intensity across the image, (which can be assumed for now to be the average value across the object of interest). This becomes a matter of photon acquisition time.

Apparatuses, methods, and systems for providing such modal imaging techniques are discussed in detail below. Accordingly, in the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that mechanical, electrical, and/or process changes may be made without departing from the scope of the present disclosure.

As will be appreciated, elements shown in the various embodiments herein can be added, exchanged, combined, and/or eliminated so as to provide a number of additional embodiments to the present disclosure. The proportion and the relative scale of the elements provided in the figures are intended to illustrate the embodiments of the present disclosure and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits.

As used herein, "a" or "a number of" something can refer to one or more such things, while "a plurality of" something can refer to more than one such things. For example, "a number of components" can refer to one or more components, while "a plurality of components" can refer to more than one component.

FIG. 1 illustrates an endoscopic modal imaging system in accordance with one or more embodiments of the present disclosure. The embodiment of FIG. 1 includes an endoscopic modal imaging system 100 having of a light source 101, a fiber optic 102 directing light from that light source to the region of interest 103, and a multimode fiber 104 collecting reflected or fluorescenced light from the region of interest.

Such an embodiment can also include a spatial mode demultiplexer 105, that impresses the radiation upon a waveguide which separates out its modes to separate photon detectors 106.

The output of the spatial mode demultiplexer 105 is deconvoluted, if necessary, using the transfer matrix method to eliminate the mode mixing. As used herein, "deconvoluting" refers to the process of reversing optical distortion effects of an imaging instrument.

The output of the one or more photon detectors 106 forming a photodetection array is fed into a processor (e.g., of computing device 107), whereby the image matrix is solved by inverting the basis functions $$I=[P_Q]^{-1}S[P_R]^{-1}$$

In one embodiment, the energy level of each mode can be measured using one or more photo detectors placed at the end of the fiber. The type of photo detector to be used can be determined by the intensity of the incoming light. For example, for dim sources, it may be necessary to utilize single photon detectors, but for bright sources conventional low noise detectors are adequate.

The output of the detectors forms a modal distribution which is then analyzed by the computing device 107 to discern the image from which it originated. Detectors may range from the exotic, such as superconducting nanowire single photon detector (SNSPD), to conventional optical and IR photon detector semiconductor technologies, such as an avalanche photo diode (APD). Mid-wave infrared detectors (MWIRs) can also be used. In various embodiments, one detector may be utilized for each mode pair (q, r).

To realize the modal surface, the incoming radiation beam must be separated by mode pair (q, r). Mode demultiplexing is an intense area of research and has been demonstrated for use in the fields of silicon photonic integrated circuits, quantum computing, as well as in astrophotonics. The figures provided herein illustrate embodiments of how such a system could be designed to provide mode demultiplexing and image capture.

Of particular relevance are those techniques that the separate the Hermite Gaussian or Laguerre Gauss polynomial modes in dielectric waveguides. Known techniques for sorting modes of this type include: mode-separating fiber photonic lanterns, mode-dependent Y-junction power splitters in thin film optical waveguides, multimode interference couplers, and mode-dependent scattering by photonic crystals or random scatters.

Depending upon the method of mode sorting, "speckle" patterns produced by the "random" scattering of coherent light can result. However, these patterns are in fact deterministic and repeatable. Accordingly, by imposing the appropriate phase mask on the light before it is incident on such a scatterer, one can force the "speckle" pattern to approximate a single bright spot at a specific location. However, this arrangement will only be correct for one specific mode.

As different spatial modes have different spatial phase distributions, a particular mask will only work for one special distribution. Accordingly, a different mask can force another mode to produce a bright spot elsewhere, and so on. In such an embodiment, the complex nature of the scattering means the masks can be found by "trial and error" using genetic algorithms.

Figure 2:
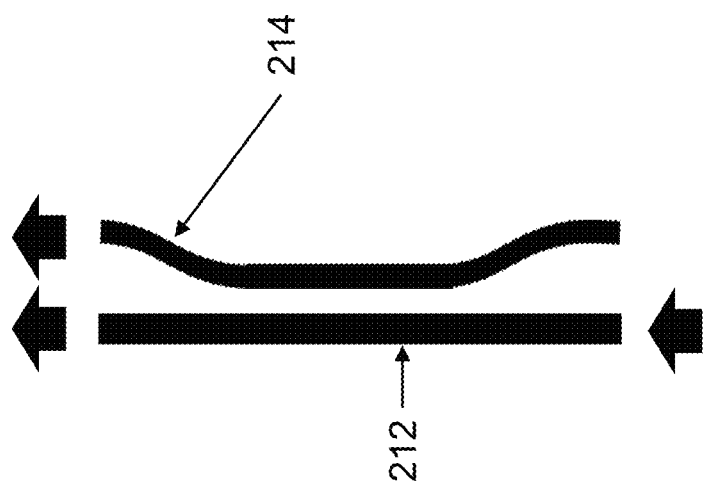
FIG. 2 illustrates some optional mode separating implementations for use in a modal imaging system in accordance with one or more embodiments of the present disclosure.
Figure 2:
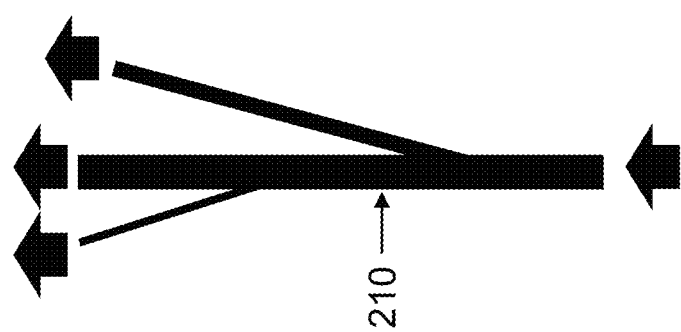

FIG. 2 illustrates some optional mode separating implementations for use in a modal imaging system in accordance with one or more embodiments of the present disclosure. In the examples shown in FIG. 2, a first arrangement is shown on the left side of the figure and a second arrangement is shown on the right side of the figure.

Generally speaking, the most basic mode separators rely on either branching or coupling architectures. In the first arrangement of FIG. 2, an asymmetric branching waveguide 210 with shallow taper between the main part of the waveguide and the branches has been shown to separate out modes. The slow taper enables adiabatic passage and avoids the architecture from merely acting as a power splitter.

In the second arrangement, a second waveguide 214 is put in close proximity to the first waveguide 212. Over the region, where the two waveguides are in close proximity, the electromagnetic wave will couple back and forth between guides according to the phase. If the proper coupling length between the two waveguides is utilized, the transfer to the second waveguide can be near 100%.

Figure 3:
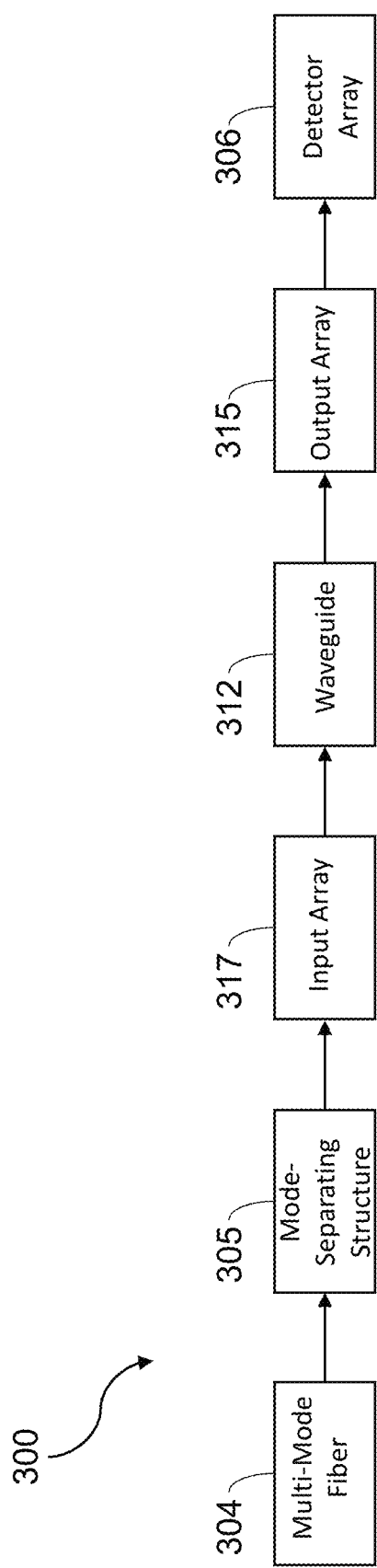
FIG. 3 illustrates a modal imaging system in accordance with one or more embodiments of the present disclosure.

FIG. 3 illustrates a modal imaging system 300 in accordance with one or more embodiments of the present disclosure. As shown in FIG. 3, a modal imaging system 300 may include a multi-mode fiber 304 provided to receive incoming radiation, a mode separating structure 305 for separating the received incoming radiation into multiple modes, and at least one output array 315. The output array 315 may, for example, have grating elements (e.g., diffraction grating) and a detector array for measuring an energy level of each mode to construct an image of the received incoming radiation. The system 300 may also include an input imaging array 317. Each mode of radiation may be routed through a waveguide 312 from elements of the input imaging array 317 to elements of the output array 315. The radiation may then be directed from the output array 315 to one or more elements of a detector array 306.

Another method of mode separation can also be utilized in some embodiments. Through the control of strongly scattering processes (i.e., wave front shaping through a complex medium), it is possible to separate an image source into modes. In this method, by placing an optimized phase structure onto the input light field, the scattering media custom-tailor the sorting process with respect to the number and type of input spatial light modes.

Through use of such embodiments, radiation directed through a multi-mode fiber can be imaged at a sub-diffraction resolution. Such advancements will enable significant improvements in imaging devices from microscopes to telescopes, among other aperture-based devices.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The invention claimed is:

1. A modal imaging system, comprising:
    a multi-mode fiber provided to receive incoming radiation;
    a mode separating structure configured to receive the incoming radiation from the multi-mode fiber and separate the received incoming radiation into multiple modes; and
    one or more detector elements for measuring an energy level of each mode to construct an image of the received incoming radiation.

2. The system of claim 1, wherein the system includes one a light source near an end of the multi-mode fiber.

3. The system of claim 1, wherein the mode separating structure is a spatial mode demultiplexer.

4. The system of claim 1, wherein a number of the one or more detector elements can form one or more detector arrays.

5. The system of claim 1, wherein one or more optical waveguides connect elements of an input imaging array to elements of an output array.

6. The system of claim 1, wherein the mode separating structure is configured to separate the received incoming radiation into multiple modes.

7. The system of claim 1, wherein an end of the multi-mode fiber is configured to be placed to image an inner portion of a patient's body.

8. The system of claim 1, wherein the mode separating structure is formed from a branching waveguide.

9. The system of claim 1, wherein the mode separating structure is formed from two waveguides.

10. A modal imaging system, comprising:
    a multi-mode fiber provided to receive incoming radiation;
    a mode separating structure for separating the received incoming radiation into multiple modes; and
    a detector array having multiple array elements for measuring an energy level of each mode to construct an image of the received incoming radiation.

11. The system of claim 10, wherein the system further includes an input imaging array.

12. The system of claim 10, wherein an end of the multi-mode fiber is configured to be placed to image an inner portion of a patient's body.

13. A modal imaging method, comprising:
    collecting incoming radiation with a multi-mode fiber;
    separating an output of the multi-mode fiber into multiple modes; and
    measuring an energy level of each mode to construct an image of the received incoming radiation.

14. The method of claim 13, wherein the method further comprises assigning the energy of each distribution to the average mode of each distribution to reconstruct the image.

15. The method of claim 13, wherein the method includes deconvoluting the output of the multi-mode fiber.

16. The method of claim 15, wherein the output of the multi-mode fiber is deconvoluted using the transfer matrix method.

17. The method of claim 13 wherein the method further includes emitting light onto a portion of a patient's body that is to be imaged.

18. The method of claim 13, wherein the method further comprises routing each mode of radiation through a waveguide from input imaging array elements to output array elements.

19. The method of claim 18, wherein the method further comprises directing the radiation from the output array elements to one or more detector array elements.

20. The method of claim 13, wherein the method further comprises analyzing a modal distribution to construct an image from which the modal distribution originated, wherein the modal distribution is an output of one or more photon detectors placed at an end of the multi-mode fiber.

* * * * *